US010488318B2

(12) United States Patent
Ascheman

(10) Patent No.: US 10,488,318 B2
(45) Date of Patent: Nov. 26, 2019

(54) TARGET-ANALYTE PERMEATION TESTING INSTRUMENT WITH SENSOR FEED LINE CONDITIONING SYSTEM

(71) Applicant: MOCON, INC., Minneapolis, MN (US)

(72) Inventor: Timothy A. Ascheman, Elk River, MN (US)

(73) Assignee: MOCON, INC., Minneapolis, MN (US)

( * ) Notice: Subject to any disclaimer, the term of this patent is extended or adjusted under 35 U.S.C. 154(b) by 261 days.

(21) Appl. No.: 15/100,448

(22) PCT Filed: Feb. 24, 2015

(86) PCT No.: PCT/US2015/017196
§ 371 (c)(1),
(2) Date: May 31, 2016

(87) PCT Pub. No.: WO2015/127415
PCT Pub. Date: Aug. 27, 2015

(65) Prior Publication Data
US 2016/0299049 A1 Oct. 13, 2016

Related U.S. Application Data

(60) Provisional application No. 61/943,772, filed on Feb. 24, 2014.

(51) Int. Cl.
*G01N 15/08* (2006.01)
*G01N 35/00* (2006.01)
*G01N 33/00* (2006.01)
*G01N 35/10* (2006.01)

(52) U.S. Cl.
CPC ..... *G01N 15/0826* (2013.01); *G01N 15/0806* (2013.01); *G01N 33/004* (2013.01); *G01N 35/00693* (2013.01); *G01N 35/00712* (2013.01); *G01N 35/1097* (2013.01); *G01N 2015/086* (2013.01)

(58) Field of Classification Search
CPC .................. G01N 15/0826; G01N 2015/086
USPC ........................................................ 73/38
See application file for complete search history.

(56) References Cited

U.S. PATENT DOCUMENTS

| 3,498,110 A | 3/1970 | Brun |
| 3,590,634 A | 7/1971 | Pasternak et al. |
| 3,618,361 A | 11/1971 | Stephens et al. |
| 4,464,927 A | 8/1984 | Reid |

(Continued)

FOREIGN PATENT DOCUMENTS

| CA | 2432452 A1 | 6/2002 |
| EP | 2113764 A2 | 11/2009 |

(Continued)

OTHER PUBLICATIONS

"Thermo Environmental Instruments Model 48C Trace Level Gas Filter Correlation Carbon Monoxide Analyzer", Standard Operating Procesures, SOP Version No. 2.0, May 6, 2009, p. 1-32.

(Continued)

*Primary Examiner* — John Fitzgerald
(74) *Attorney, Agent, or Firm* — Sherrill Law Offices, PLLC

(57) ABSTRACT

A target-analyte permeation testing instrument (10) characterized by a sensor feed line ($300_nB_{out}$ and $300_S$) conditioning system.

2 Claims, 1 Drawing Sheet

(56) References Cited

U.S. PATENT DOCUMENTS

| | | | |
|---|---|---|---|
| 4,656,865 A | | 4/1987 | Callan |
| 4,667,153 A | | 5/1987 | Doyle |
| 4,791,822 A | * | 12/1988 | Penny .................. E21B 43/267 73/38 |
| 4,852,389 A | * | 8/1989 | Mayer .................. G01N 15/08 73/38 |
| 4,922,758 A | * | 5/1990 | Penny .................. E21B 43/267 73/38 |
| 4,944,180 A | | 7/1990 | Tou et al. |
| 5,088,316 A | * | 2/1992 | McKelvey ............. G01N 15/08 73/38 |
| 5,107,696 A | * | 4/1992 | Mayer .................. G01N 15/08 73/38 |
| 5,361,625 A | | 11/1994 | Ylvisaker |
| 6,066,243 A | | 5/2000 | Anderson et al. |
| 7,178,384 B2 | | 2/2007 | Bujas et al. |
| 7,571,749 B2 | | 8/2009 | Stochi |
| 7,578,208 B2 | | 8/2009 | Mayer |
| 7,818,996 B2 | * | 10/2010 | Gevers ................. B01D 65/102 73/38 |
| 8,821,614 B1 | * | 9/2014 | Albenze ................ B01D 53/22 73/37 |
| 2002/0045243 A1 | | 4/2002 | Laska et al. |
| 2003/0019747 A1 | | 1/2003 | Saffell et al. |
| 2003/0074945 A1 | | 4/2003 | Engle et al. |
| 2003/0074954 A1 | * | 4/2003 | Engle ................. G01N 15/0826 73/38 |
| 2004/0040372 A1 | * | 3/2004 | Plester ............... G01N 15/0826 73/38 |
| 2005/0211572 A1 | | 9/2005 | Buck et al. |
| 2007/0271998 A1 | * | 11/2007 | Woolfenden ....... G01N 15/0826 73/38 |
| 2008/0028834 A1 | * | 2/2008 | Gevers ................. B01D 65/102 73/38 |
| 2008/0060417 A1 | * | 3/2008 | DeRoos ............. G01N 15/0826 73/38 |
| 2008/0060418 A1 | | 3/2008 | DeRoos et al. |
| 2010/0054998 A1 | | 3/2010 | Mayer et al. |
| 2010/0223979 A1 | | 9/2010 | Ploehn et al. |
| 2010/0274515 A1 | | 10/2010 | Hoss et al. |
| 2012/0262298 A1 | | 10/2012 | Bohm et al. |
| 2012/0330596 A1 | | 12/2012 | Kouznetsov |
| 2014/0238101 A1 | | 8/2014 | Mealy, Jr. et al. |
| 2017/0072157 A1 | | 3/2017 | Tolmie et al. |

FOREIGN PATENT DOCUMENTS

| | | |
|---|---|---|
| JP | 62165545 A | 7/1987 |
| JP | 63236943 A | 10/1988 |
| JP | 200572110 A | 3/2005 |
| JP | 2006094838 A | 4/2006 |
| WO | 98/03868 | 1/1998 |
| WO | 2010029282 A2 | 4/2001 |
| WO | 2013143029 A1 | 3/2013 |

OTHER PUBLICATIONS

Beyer, David Stewart; "Industrial Accident Prevention"; Book; Houghton Mifflin Company, Boston and New York; 1916.

* cited by examiner

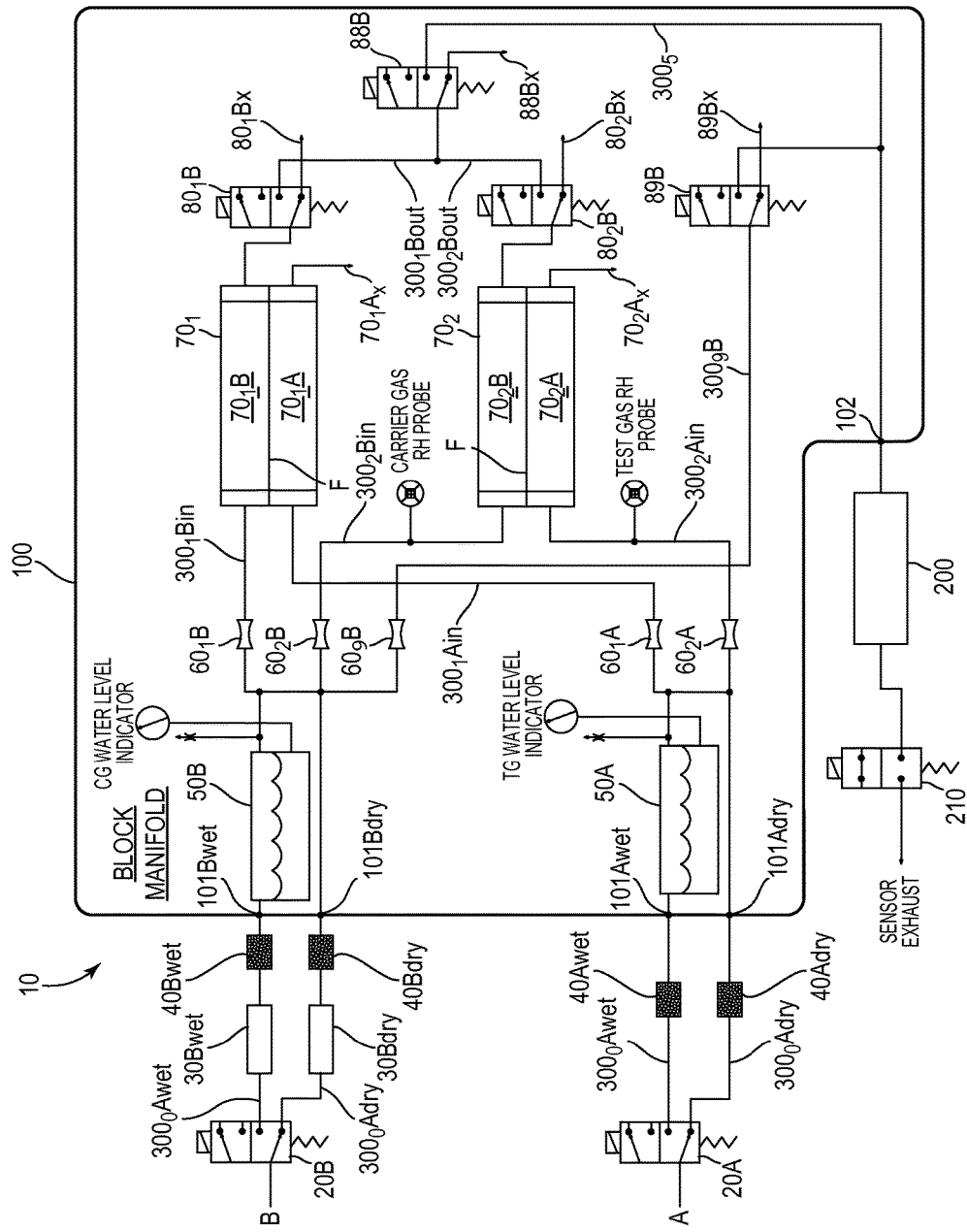

TARGET-ANALYTE PERMEATION TESTING INSTRUMENT WITH SENSOR FEED LINE CONDITIONING SYSTEM

BACKGROUND

Permeation instruments are used to measure the transmission rate of a target analyte, such as oxygen, carbon dioxide or water vapor, through various samples, such as membranes, films, envelopes, bottles, packages, containers, etc. (hereinafter collectively referenced as "test films" for convenience). Typical test films are polymeric packaging films such as those constructed from low density polyethylene (LDPE), high density polyethylene (HDPE), oriented polypropylene (OPP), polyethylene terepthalate (PET), polyvinylidene chloride (PVTDC), etc. Typically, the film to be tested is positioned within a test chamber to sealing separate the chamber into first and second chambers. The first chamber (commonly referenced as the driving or analyte chamber) is filled with a gas containing a known concentration of the target analyte (commonly referenced as a driving gas). The second chamber (commonly referenced as the sensing chamber) is flushed with an inert gas (commonly referenced as a carrier gas) to remove any target analyte from the cell. A sensor for the target analyte is placed in fluid communication with the sensing chamber for detecting the presence of target analyte that has migrated into the sensing chamber from the driving chamber through the test film. Exemplary permeation instruments for measuring the transmission rate of oxygen ($O_2$), carbon dioxide ($CO_2$) and water vapor ($H_2O$) through test films are commercially available from Mocon, Inc. of Minneapolis, Minn. under the designations OXTRAN, PERMATRAN-C and PERMATRAN-W, respectively.

Permeation testing instruments employ a very low mass flow through rate through the instrument to limit the creation of any pressure differentials in the instrument that could impact humidification of the test and/or carrier gases or create a pressure-induced driving force across a test film. This low mass flow rate through the instrument imposes a significant time delay between measurements from different testing cells as the feed line to the sensor is flushed with the carrier gas from the sensing chamber of the newly selected testing cell.

A substantial need exists for a permeation instrument capable of contemporaneously measuring target-analyte transmission rates from a plurality of testing cells with minimal changeover time between measurements from different testing cells.

SUMMARY OF THE INVENTION

A first aspect of the invention is a target-analyte permeation testing instrument for measuring target-analyte permeation rate of a test film in test cell, characterized by a sensor feed line conditioning system.

A first embodiment of the instrument has a target-analyte sensor and at least one test cell operable for retaining a test film in a testing chamber so as to sealingly divide the testing chamber into a driving chamber and a sensing chamber. The target-analyte permeation testing instrument is characterized by (i) a length of common conduit in fluid communication with the shared target-analyte sensor, (ii) individual dedicated lengths of conduit, each in fluid communication with the length of common conduit and each operable for delivering a fluid subjected by the instrument to a different target-analyte exposure experience, with at least one of the individual dedicated lengths of conduit in fluid communication with the sensing chamber of the at least one test cell, (iii) a dedicated valve associated with each dedicated length of conduit operable between venting and flow through states, and (iv) a common valve associated with the length of common conduit operable between venting and flow through states.

A second embodiment of the instrument has a shared target-analyte sensor and a plurality of test cells each defining a testing chamber with each test cell operable for retaining a test film to sealingly divide the testing chamber into a driving chamber and a sensing chamber. The target-analyte permeation testing instrument is characterized by (i) a length of common conduit in fluid communication with the shared target-analyte sensor, (ii) individual dedicated lengths of conduit in fluid communication with each of an associated sensing chamber and the length of common conduit, each dedicated length of conduit operable for carrying fluid from the sensing chamber of an associated test cell to the length of common conduit, (iii) a dedicated valve associated with each dedicated length of conduit operable between venting and flow through states, and (iv) a common valve associated with the length of common conduit operable between venting and flow through states.

A second aspect of the invention is a method of measuring target-analyte transmission rate through a test film utilizing a target-analyte permeation testing instrument according to the first aspect of the invention.

A first embodiment of the second aspect of the invention is a method of measuring target-analyte transmission rate through a test film utilizing a target-analyte permeation testing instrument according to the first embodiment of the first aspect of the invention. The method includes initial set-up and subsequent testing steps. The set-up steps include the steps of (i) obtaining a target-analyte permeation testing instrument according to the first embodiment of the first aspect of the invention, (ii) loading a test film into the at least one test cell, (iii) providing a flow of target-analyte containing driving gas through the driving chamber of the at least one test cell containing a test film, and (iv) providing a flow of inert carrier gas through the sensing chamber of the at least one test cell containing a test film. The testing steps includes the sequential steps of (a) measuring target-analyte concentration in the sensing chamber of the at least one test cell by setting the dedicated valve for the individual dedicated length of conduit associated with the sensing chamber of the at least one test cell to flow-through, setting the common valve to flow-through, setting all other dedicated valves to vent, and measuring concentration of target-analyte in fluid communication with the target-analyte sensor, (b) conditioning the instrument for ensuing measurement of target-analyte concentration in a fluid delivered to the common length of conduit through a different individual dedicated length of conduit for a conditioning period by setting the common valve to vent, setting the dedicated valve for the individual dedicated length of conduit associated with the sensing chamber of the at least one test cell to vent, setting the dedicate valve associated with the different individual dedicated length of conduit to flow-through, and leaving all other dedicated valves to vent, and (c) measuring target-analyte concentration in the fluid delivered to the common length of conduit through a different individual dedicated length of conduit by setting the common valve to flow-through.

A second embodiment of the second aspect of the invention is a method of simultaneously measuring target-analyte transmission rate through a plurality of test films utilizing a target-analyte permeation testing instrument according to the second embodiment of the first aspect of the invention. The method includes initial set-up and subsequent testing steps. The set-up steps include the steps of (i) obtaining a target-analyte permeation testing instrument according to the second embodiment of the first aspect of the invention, (ii) loading a test film into each of at least two test cells, (iii) providing a flow of target-analyte containing driving gas through the driving chamber of each test cell containing a test film, and (iv) providing a flow of inert carrier gas through the sensing chamber of each test cell containing a test film. The testing steps includes the sequential steps of (a) measuring target-analyte concentration in the sensing chamber of a first test cell by setting the associated dedicate valve to flow-through, setting the common valve to flow-through, setting all other dedicated valves to vent, and measuring concentration of target-analyte in fluid communication with the target-analyte sensor, (b) conditioning the instrument for ensuing measurement of target-analyte concentration in the sensing chamber of a second test cell for a conditioning period by setting the common valve to vent, setting the dedicated valve associated with the sensing chamber of the first test cell to vent, setting the dedicate valve associated with the sensing chamber of the second test cell to flow-through, and leaving all other dedicated valves to vent, and (c) measuring target-analyte concentration in the sensing chamber of the second test cell by setting the common valve to flow-through.

BRIEF DESCRIPTION OF THE DRAWINGS

FIG. 1 is a schematic plumbing diagram of one embodiment of the invention.

DETAILED DESCRIPTION OF A PREFERRED EMBODIMENT

Nomenclature Table

| | |
|---|---|
| 10 | Target-Analyte Permeation Testing Instrument |
| 20A | Test Gas RH Control Valve |
| 20B | Carrier Gas RH Control Valve |
| $30B_{wet}$ | Catalyst Chamber in Wet Carrier Gas Line |
| $30B_{dry}$ | Catalyst Chamber in Dry Carrier Gas Line |
| $40A_{wet}$ | Particle Filter in Wet Test Gas Line |
| $40A_{dry}$ | Particle Filter in Dry Test Gas Line |
| $40B_{wet}$ | Particle Filter in Wet Carrier Gas Line |
| $40B_{dry}$ | Particle Filter in Dry Carrier Gas Line |
| 50A | Water Reservoir for Test Gas |
| 50B | Water Reservoir for Carrier Gas |
| $60_n$ | Capillary Restrictors |
| $60_1A$ | Capillary Restrictor for Test Gas Channel to First Test Cell |
| $60_2A$ | Capillary Restrictor for Test Gas Channel to Second Test Cell |
| $60_1B$ | Capillary Restrictor for Carrier Gas Channel to First Test Cell |
| $60_2B$ | Capillary Restrictor for Carrier Gas Channel to Second Test Cell |
| $60_9B$ | Capillary Restrictor for Carrier Gas Channel to Rezero Valve |
| $70_n$ | Testing Cells |
| $70_nA$ | Driving Chamber of Test Cell n |
| $70_nB$ | Sensing Chamber of Test Cell n |
| $70_nAx$ | Exhaust from Driving Chamber of Test Cell n |
| $70_1$ | First Testing Cells |
| $70_1A$ | Driving Chamber of First Test Cell |
| $70_1Ax$ | Exhaust from Driving Chamber of First Test Cell |
| $70_1B$ | Sensing Chamber of First Test Cell |
| $70_2$ | Second Testing Cells |
| $70_2A$ | Driving Chamber of Second Test Cell |
| $70_2Ax$ | Exhaust from Driving Chamber of Second Test Cell |
| $70_2B$ | Sensing Chamber of Second Test Cell |
| $80_nB$ | Carrier Gas Sensing Chamber Exit Valve for Testing Cell n |
| $80_1B$ | First Test Cell Carrier Gas Exit Valve |
| $80_1Bx$ | Exhaust from Sensing Chamber of First Test Cell |
| $80_2B$ | Second Test Cell Carrier Gas Exit Valve |
| $80_2Bx$ | Exhaust from Sensing Chamber of Second Test Cell |
| 88B | Common Channel Conditioning Valve |
| 88Bx | Exhaust from Common Channel Conditioning Valve |
| 89B | Rezero Valve |
| 89Bx | Exhaust from Rezero Valve |
| 100 | Block Manifold |
| $101A_{wet}$ | Test Gas Water Reservoir Inlet Port |
| $101A_{dry}$ | Test Gas Water Reservoir Bypass Inlet Port |
| $101B_{wet}$ | Carrier Gas Water Reservoir Inlet Port |
| $101B_{dry}$ | Carrier Gas Water Reservoir Bypass Inlet Port |
| 102 | Carrier Gas Outlet Port to Sensor |
| 200 | Target-Analyte Sensor |
| 210 | Sensor Exhaust Valve |
| $300_n$ | Gas Flow Line n |
| $300_0A_{wet}$ | Test Gas Water Reservoir Inlet Line |
| $300_0A_{dry}$ | Test Gas Water Reservoir Bypass Inlet Line |
| $300_0B_{wet}$ | Carrier Gas Water Reservoir Inlet Line |
| $300_0B_{dry}$ | Carrier Gas Water Reservoir Bypass Inlet Line |
| $300_1A_{in}$ | Test Gas First Testing Cell Inlet Line |
| $300_1B_{in}$ | Carrier Gas First Testing Cell Inlet Line |
| $300_2A_{in}$ | Test Gas Second Testing Cell Inlet Line |
| $300_2B_{in}$ | Carrier Gas Second Testing Cell Inlet Line |
| $300_nB_{out}$ | Carrier Gas Outlet Line for Testing Cell n |
| $300_1B_{out}$ | Carrier Gas First Testing Cell Outlet Line |
| $300_2B_{out}$ | Carrier Gas Second Testing Cell Outlet Line |
| $300_5$ | Shared Carrier Gas Testing Cell Outlet Line |
| $300_9B$ | Carrier Gas Rezero Line |
| A | Driving or Test Gas Source |
| B | Inert or Carrier Gas Source |
| F | Test Film |

Description

Referring generally to FIG. 1, the invention is a target-analyte permeation testing instrument 10 characterized by a sensor feed line conditioning system.

The instrument 10 has a target-analyte sensor 200 and a plurality of test cells $70_n$ for measuring target-analyte permeation rate of test films $F_n$. Each test cell $70_n$ defines a testing chamber and is operable for retaining a test film F to sealingly divide the testing chamber into a driving chamber $70_nA$ and a sensing chamber $70_nB$. The cells $70_n$ are preferably secured to a block manifold 100, preferably a solid block cast metal manifold 100 into which the appropriate channels and compartments are formed. A plurality of channels $300_n$ are in fluid communication with the testing chamber of each cell $70_n$, a pressurized source of driving gas A, a pressurized source of inert gas B, and a target-analyte sensor 200. The plurality of channels $300_n$ are configured and arranged to selectively carry driving gas from the pressurized source of driving gas A to the driving chamber $70_nA$ of each cell $70_n$, carry driving gas from the driving chamber $70_nA$ of each cell $70_n$ to a driving gas exit port $70_nAx$, selectively carry inert gas from the pressurized source of inert gas B to the sensing chamber $70_nB$ of each cell $70_n$, and selectively carry inert gas from the sensing chamber $70_nB$ of each cell $70_n$ to a the target-analyte sensor 200.

The instrument 10 can include a refillable first water reservoir 50A in selective fluid communication with the source of driving gas A and in fluid communication with the driving chamber $70_nA$ of each cell $70_n$, and a second refillable water reservoir 50B in selective fluid communication with the source of inert gas B and in fluid communication with the sensing chamber $70_nB$ of each cell $70_n$.

An exemplary two-cell embodiment of the invention 10 employing the optional block manifold 100 is depicted in FIG. 1. The permeation testing instrument 10 preferably includes humidification systems for each of the test gas and carrier gas, such as described in U.S. Pat. Nos. 7,578,208 and 7,908,936, the disclosures of which are hereby incorporated by reference.

A source of dry test gas A fluidly communicates with a first humidification system that includes a wet line $300_0A_{wet}$ in fluid communication with a water reservoir 50A and a dry line $300_0A_{dry}$ that bypasses the water reservoir 50A. A test gas RH control valve 20A controls flow of test gas through the wet line $300_0A_{wet}$ and dry line $300_0A_{dry}$ according to a duty cycle for achieving the desired humidification level of the test gas.

The test gas wet line $300_0A_{wet}$ enters the block manifold 100 at inlet port $101A_{wet}$. The test gas dry line $300_0A_{dry}$ enters the block manifold 100 at inlet port $101A_{dry}$.

Upon exiting the water reservoir 50A, humidified test gas in the wet line $300_0A_{wet}$ is combined with dry test gas in the dry line $300_0A_{dry}$ and the combined test gas directed by test gas inlet lines $300_1A$ and $300_2A$ to the driving chambers $70_1A$ and $70_2A$ in the first testing cell $70_1$ and second testing cell $70_2$ respectively. Test gas flows through and exits each of the driving chambers $70_1A$ and $70_2A$ through an outlet port (unnumbered) and is vented from the block manifold at vent ports $70_1Ax$ and $70_2Ax$ respectively.

Particle filters $40A_{wet}$ and $40A_{dry}$ are preferably provided in the test gas wet line $300_0A_{wet}$ and test gas dry line $300_0A_{dry}$ respectively, for removing any entrained particulate matter from the test gas before it enters the block manifold 100.

In a similar fashion, a source of dry carrier gas B fluidly communicates with a second humidification system that includes a wet line $300_0B_{wet}$ in fluid communication with a water reservoir 50B and a dry line $300_0B_{dry}$ that bypasses the water reservoir 50B. A carrier gas RH control valve 20B controls flow of carrier gas through the wet line $300_0B_{wet}$ and dry line $300_0B_{dry}$ according to a duty cycle for achieving the desired humidification level of the carrier gas.

The carrier gas wet line $300_0B_{wet}$ enters the block manifold 100 at inlet port $101B_{wet}$. The carrier gas dry line $300_0B_{dry}$ enters the block manifold 100 at inlet port $101B_{dry}$.

Upon exiting the water reservoir 50B, humidified carrier gas in the wet line $300_0B_{wet}$ is combined with dry carrier gas in the dry line $300_0B_{dry}$ and the combined carrier gas directed by carrier gas inlet lines $300_1B$ and $300_2B$ to the sensing chambers $70_1B$ and $70_2B$ in the first testing cell $70_1$ and second testing cell $70_2$ respectively. Carrier gas flows through and exits each of the sensing chambers $70_1B$ and $70_2B$ through an outlet port (unnumbered) and is directed by dedicated outlet channels $300_1B_{out}$ and $300_2B_{out}$ respectively, to a common channel $300_5$ in fluid communication with a target-analyte sensor 200 located external to the block manifold 100.

Common channel $300_5$ exits the block manifold 100 at outlet port 102.

Particle filters $40b_{wet}$ and $40b_{dry}$ are preferably provided in the carrier gas wet line $300_0B_{wet}$ and carrier gas dry line $300_0B_{dry}$ respectively, for removing any entrained particulate matter from the carrier gas before it enters the block manifold 100.

Target-analyte catalytic converters $30b_{wet}$ and $30b_{dry}$ are preferably provided in the carrier gas wet line $300_0B_{wet}$ and carrier gas dry line $300_0B_{dry}$ respectively, for converting any target-analyte in the carrier gas (e.g., $O_2$) to a molecular species (e.g., $H_2O$ when the target analyte is $O_2$) that will not be detected by the target-analyte sensor 200.

Capillary restrictors $60_1A$, $60_2A$, $60_1B$ and $60_2B$ are preferably provided in the test gas inlet lines $300_1A$ and $300_2A$, and carrier gas inlet lines $300_1B$ and $300_2B$ respectively, for facilitating a consistent and equal flow of gas into the driving chambers $70_1A$ and $70_2A$ of the testing cells $70_1$ and $70_2$, and the sensing chambers $70_1B$ and $70_2B$ of the testing cells $70_1$ and $70_2$ respectively. The capillary restrictors $60_n$ are preferably side mounted onto the block manifold 100.

Valves $80_1B$ and $80_2B$ are provided in the dedicated outlet channels $300_1B_{out}$ and $300_2B_{out}$ respectively, for selectively and mutually exclusively allowing passage of carrier gas, containing any target-analyte that has permeated through the test film F, from each of the sensing chambers $70_1B$ and $70_2B$ into sensing engagement with the sensor 200. When closed, the valves $80_1B$ and $80_2B$ vent carrier gas, containing any target-analyte that has permeated through the test film F, to atmosphere through vent ports $80_1Bx$ and $80_2Bx$ in the manifold 100. The valves $80_nB$ are preferably side mounted onto the block manifold 100.

As referenced previously, permeation testing instruments 10 employ a very low mass flow through rate through the instrument 10 to limit the creation of any pressure differentials in the instrument 10 that could impact humidification of the test and/or carrier gases or create a pressure-induced driving force across a test film F. In the embodiment depicted in FIG. 1, this low mass flow rate through the instrument 10 imposes a significant time delay between measurements from different testing cells $70_n$ as both the "stale" carrier gas contained in the length of the testing cell outlet line $300_nB_{out}$ for the upcoming testing cell $70_n$ to be measured and the "inapplicable" carrier gas contained in the length of the shared outlet line $300_5$ from the previously measured testing cell $70_n$ is flushed from the lines and replaced with fresh carrier gas, containing any target-analyte that has permeated through the test film F, from the upcoming testing cell $70_n$. The channel conditioning feature employs a common channel conditioning valve 88B in the shared outlet line $300_5$ for allowing, in coordination with opening and closing of valves $80_nB$ for the upcoming and previous testing cells $70_n$, for advanced venting of "stale" carrier gas contained in the length of the outlet line $300_nB_{out}$ for the upcoming testing cell $70_n$. The common channel conditioning valve 88B is operable as between a flow-through state, in which carrier gas is directed to the sensor 200, and a vent state, in which carrier gas is vented to atmosphere through a vent port 88Bx in the block manifold 100. The common channel conditioning valve 88B is preferably side mounted to the block manifold 100.

The instrument 10 depicted in FIG. 1 includes an optional rezero feature. Rezero is a method of measuring residual target-analyte contained in the carrier gas during performance of testing that includes the steps of bypassing the test cell(s) $70n$ and directly measuring the carrier gas target-analyte level, which is then subtracted from the measured transmission rate of the target-analyte level for each sample.

The rezero feature includes a rezero line $300_9B$ upstream from the testing cells $70_n$ for bypassing the testing cells $70_n$ and carrying carrier gas directly to the sensor 200. A rezero valve 89B is provided in the rezero line $300_9B$ for selectively directing carrier gas to the sensor 200 or venting carrier gas from the block manifold 100 at vent port 89Bx. The rezero valve 89B is preferably side mounted to the block manifold 100.

A capillary restrictor $60_9B$ is preferably provided in the carrier gas rezero line $300_9B$ for facilitating a consistent and equal flow of carrier gas into the sensing chambers $70_1B$ and $70_2B$ of the testing cells $70_1$ and $70_2$ respectively. The capillary restrictor $60_9B$ is, as with the other capillary restrictors, preferably side mounted onto the block manifold 100.

The sensor 200 is selected to measure the appropriate target-analyte (e.g., oxygen ($O_2$), carbon dioxide ($CO_2$) or water vapor ($H_2O$)). Selection of a suitable sensor 200 is well within the knowledge and expertise of a person having routine skill in the art. The sensor 200 is preferably a coulox sensor and is equipped with an exhaust valve 210 for preventing atmospheric contamination of the sensor when there is no flow of carrier gas to the sensor 200.

Use

Relatively rapid contemporaneous measurement of target-analyte transmission rate through a plurality of test films F can achieved with the target-analyte permeation testing instrument 10. The method includes initial set-up and subsequent testing steps.

The set-up steps include (i) obtaining a target-analyte permeation testing instrument 10 in accordance with the invention, (ii) loading a test film F into each of at least two testing cells $70_n$, (iii) providing a flow of target-analyte containing driving gas through the driving chamber $70_nA$ of each testing cell $70_n$ containing a test film F, and (iv) providing a flow of inert carrier gas through the sensing chamber $70_nB$ of each testing cell $70_n$ containing a test film F.

Based upon the embodiment depicted in FIG. 1, the testing steps includes the sequential steps of (a) measuring target-analyte concentration in the sensing chamber $70_1B$ of a first testing cell $70_1$ by setting the associated dedicate valve $80_1B$ to flow-through, setting the common channel valve 88B to flow-through, setting all other dedicated valves $80_2B$ to vent, and measuring concentration of target-analyte in fluid communication with the target-analyte sensor 200, (b) conditioning the instrument 10 for ensuing measurement of target-analyte concentration in the sensing chamber $70_2B$ of a second testing cell $70_2$ for a conditioning period by setting the common channel valve 88B to vent, setting the dedicated valve $80_1B$ associated with the sensing chamber $70_1B$ of the first testing cell $70_1$ to vent, setting the dedicate valve $80_2B$ associated with the sensing chamber $70_2B$ of the second test cell $70_2$ to flow-through, and leaving all other dedicated valves (none depicted in the embodiment of FIG. 1) to vent, and (c) measuring target-analyte concentration in the sensing chamber $70_2B$ of the second test cell $70_2$ by setting the common channel valve 88B to flow-through.

I claim:

1. A target-analyte permeation testing instrument for measuring target-analyte permeation rate of a test film in a test cell, the instrument having (–) a target-analyte sensor, and (–) at least one test cell operable for retaining a test film in a testing chamber so as to sealingly divide the testing chamber into a driving chamber and a sensing chamber, the target-analyte permeation testing instrument characterized by (i) a length of common conduit in fluid communication with the shared target-analyte sensor, (ii) individual dedicated lengths of conduit, each in fluid communication with the length of common conduit and each operable for delivering a fluid subjected by the instrument to a different target-analyte exposure experience, with at least one of the individual dedicated lengths of conduit in fluid communication with the sensing chamber of the at least one test cell, (iii) a dedicated valve associated with each dedicated length of conduit operable between venting and flow through states, and (iv) a common valve associated with the length of common conduit operable between venting and flow through states.

2. A method of simultaneously measuring target-analyte transmission rate through a plurality of test films utilizing the target-analyte permeation testing instrument of claim 1, comprising the steps of:
 (a) obtaining a target-analyte permeation testing instrument according to claim 1,
 (b) loading a test film into each of at least two test cells,
 (c) providing a flow of target-analyte containing driving gas through the driving chamber of each test cell containing a test film, and
 (d) providing a flow of inert carrier gas through the sensing chamber of each test cell containing a test film, followed by the sequential steps of:
 (e) measuring target-analyte concentration in the sensing chamber of a first test cell by setting the associated dedicate valve to flow-through, setting the common valve to flow-through, setting all other dedicated valves to vent, and measuring concentration of target-analyte in fluid communication with the target-analyte sensor,
 (f) conditioning the instrument for ensuing measurement of target-analyte concentration in the sensing chamber of a second test cell for a conditioning period by setting the common valve to vent, setting the dedicated valve associated with the sensing chamber of the first test cell to vent, setting the dedicate valve associated with the sensing chamber of the second test cell to flow-through, and leaving all other dedicated valves to vent, and
 (g) measuring target-analyte concentration in the sensing chamber of the second test cell by setting the common valve to flow-through.

* * * * *